(12) United States Patent
Duncan

(10) Patent No.: US 6,604,528 B1
(45) Date of Patent: Aug. 12, 2003

(54) ACID REFLUX AND SNORING DEVICE

(76) Inventor: Lloyd P. Duncan, 722 Connemara Ct., Venice, FL (US) 34292

( * ) Notice: Subject to any disclaimer, the term of this patent is extended or adjusted under 35 U.S.C. 154(b) by 0 days.

(21) Appl. No.: 10/131,432

(22) Filed: Apr. 22, 2002

(51) Int. Cl.7 .................................................. A61F 5/56
(52) U.S. Cl. ........................ 128/848; 128/859; 602/902
(58) Field of Search ................................ 128/846, 848, 128/859–862; 602/902

(56) References Cited

U.S. PATENT DOCUMENTS

| | | | |
|---|---|---|---|
| 469,594 A | 2/1892 | Perou | |
| D31,395 S | 8/1899 | Geraghty | |
| D32,565 S | 4/1900 | Hooper | |
| 774,446 A | 11/1904 | Moulton | |
| 885,196 A | * 4/1908 | Steil | 128/848 |
| 1,483,694 A | 2/1924 | Stukey | |
| 2,627,268 A | 2/1953 | Leppich | 128/136 |
| 2,705,006 A | * 3/1955 | Ceftel | 128/848 |
| 4,170,230 A | 10/1979 | Nelson | 128/139 |
| 5,056,534 A | 10/1991 | Wright | 128/848 |
| 5,316,020 A | * 5/1994 | Truffer | 128/861 |
| 5,447,168 A | * 9/1995 | Bancroft | 128/859 |
| 5,642,738 A | 7/1997 | Lilly, Jr. | 128/848 |
| 5,921,240 A | * 7/1999 | Gall | 602/902 |

* cited by examiner

Primary Examiner—Michael A. Brown
(74) Attorney, Agent, or Firm—Gifford, Krass, Groh, Sprinkle, Anderson & Citkowski, P.C.

(57) ABSTRACT

A breathing device that is positioned within the mouth between the teeth and inner lips to prevent breathing through the mouth and direct air through the nasal passages to deter snoring. The device also acts to stimulate saliva and is provided with passages at opposite edges of the mouth to direct saliva from the area of the passages to the throat for swallowing of saliva which tend to neutralize the effects of acid reflux. The device also is provided with guide elements to position the breathing control device relative to the mouth and teeth and at the same time prevents mating of the teeth and therefore gnashing or grinding of teeth during sleep.

15 Claims, 2 Drawing Sheets

ACID REFLUX AND SNORING DEVICE

This invention relates to apparatus to control the breathing and more particularly to suppress snoring and stimulate saliva to counter acid reflux.

BACKGROUND OF THE INVENTION

Sleep disorders include acid reflux and snoring. Reflux is a normal phenomenon but can lead to gastro esophageal reflux disease (GERD) in severe cases and to heartburn in milder cases. Reflux symptoms are often treated as an acid problem and a typical remedy are antacids. Surveys show that about forty five percent suffer from heartburn at least once a month and seven percent as frequently as every day. Also, thirteen percent of adults use antacids as often as two or more times per week. Employers have complained that the annual cost of prescription medicines to alleviate the problems is a serious factor in the cost of operations.

With respect to snoring, forty five percent of normal adults snore occasionally and about twenty five percent snore habitually. Various attempts have been made to prevent snoring and hundreds of patent on the subject cover a period from the late 1800's to the present.

Although snoring and acid reflux would not seem related, both conditions are suffered commonly and both are dependent on the control of air through the mouth. In the case of snoring, air passage through the mouth is required for the condition to exist so preventing such breathing and redirecting air passage through the nose tends to inhibit snoring. At the same time swallowing requires at least limited breathing through the mouth and swallowing is required to dispose of saliva which in turn serves to neutralize reflux conditions.

SUMMARY OF THE INVENTION

It is an object of the invention to provide a device to prevent breathing through the mouth and yet permit passage of sufficient air through the mouth upon swallowing for dispersion of saliva.

Another object of the invention is to provide a simple breathing device that acts as a valve to limit air through the mouth and re-direct inhaling through the nose and at the same time permits the passage of sufficient air through the mouth during the act of swallowing the saliva that may be stimulated by the device to aid combating reflux problems.

Still another aspect is to provide a breathing device that stimulates the secretion of saliva and controls the passage of air to aid in dispersion and swallowing of the saliva as to neutralize the effects of acid reflux.

The purposes of the invention are attained by a breathing control device that acts as a valve for air passage through the mouth and is in the form of a curved sheet of flexible plastic material that is disposed in the mouth between the lips and teeth. In that position the device acts to prevent the passage of air through the mouth upon inhaling and to require air entry through the nose. The curved sheet is held in position relative to the mouth by guide elements in the form of pegs disposed in spaced relation and extending normal to the outer or convex surface of the curved sheet for disposition at the corners of the mouth. The guide pegs prevent lateral displacement and at the same time act as a handle for manipulating the device. The curved sheet of the device also is provided with a pair of openings disposed adjacent to the guide elements that extend in opposite direction from the guide pegs to form air passages when a person using the device swallows at which time the corners of the mouth open slightly to permit air passage. Pegs also are formed on the concave side of the curved sheet generally opposite of the pegs on the concave side of the curved sheet where they can be gripped between the teeth of the user and act to prevent vertical displacement of the device and at the same time prevent contact of the upper and lower teeth and therefore grinding of the teeth during sleep.

DETAILED DESCRIPTION

Figure 1:
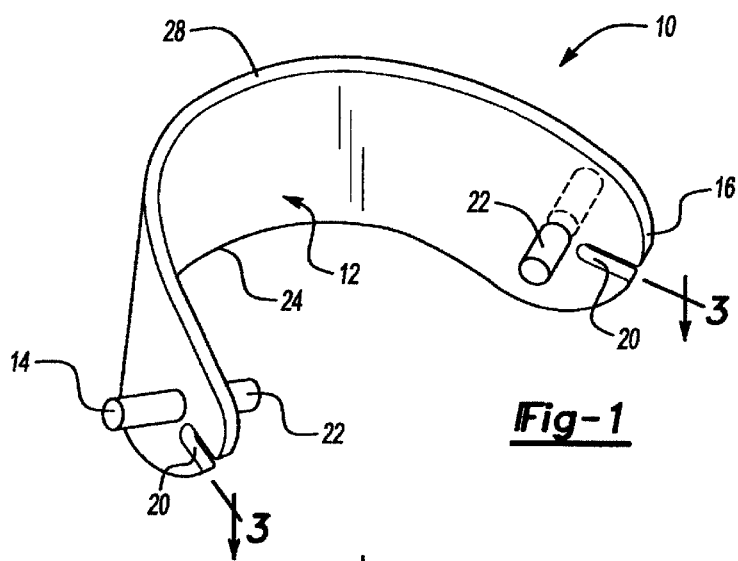
FIG. 1 is a perspective view of the breathing control device embodying the invention taken from the upper rear.
Figure 2:
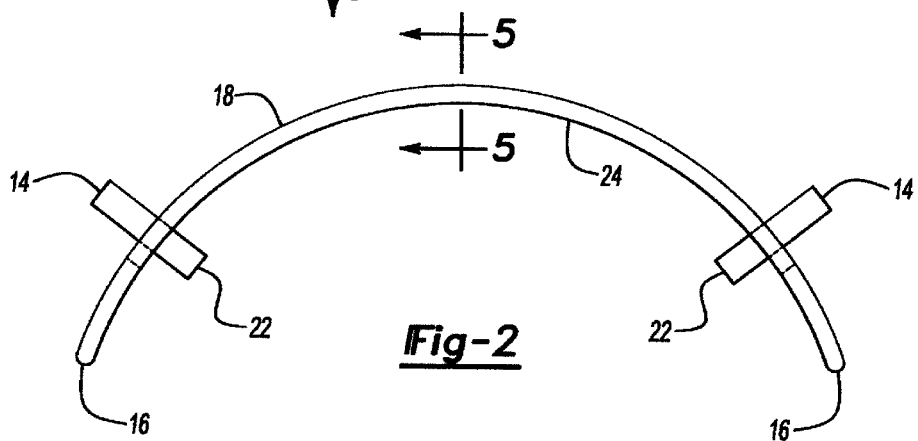
FIG. 2 is a top plan view with the breathing control device seen in FIG. 1.
Figure 3:
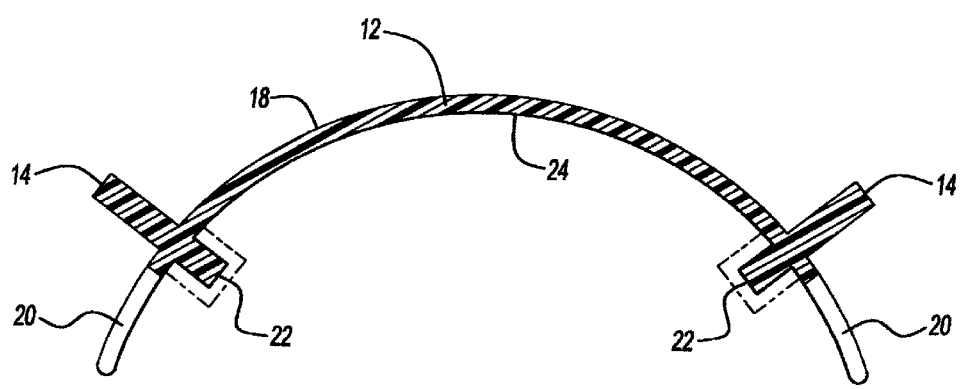
FIG. 3 is a cross-sectional view similar to the view in FIG. 2 taken on line 3—3 midway through the breathing control device in FIG. 1.
Figure 4:
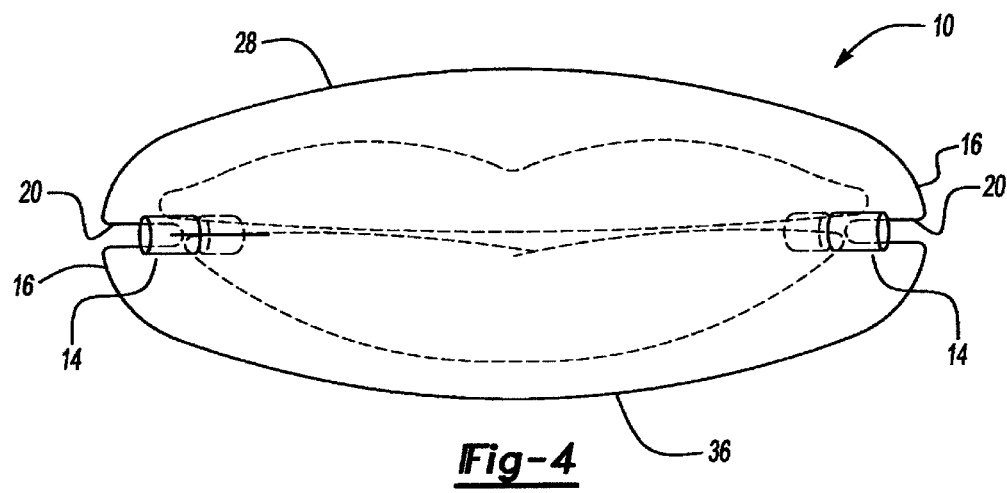
FIG. 4 is an elevational view with the outline of the mouth of a user shown in dash line.
Figure 5:
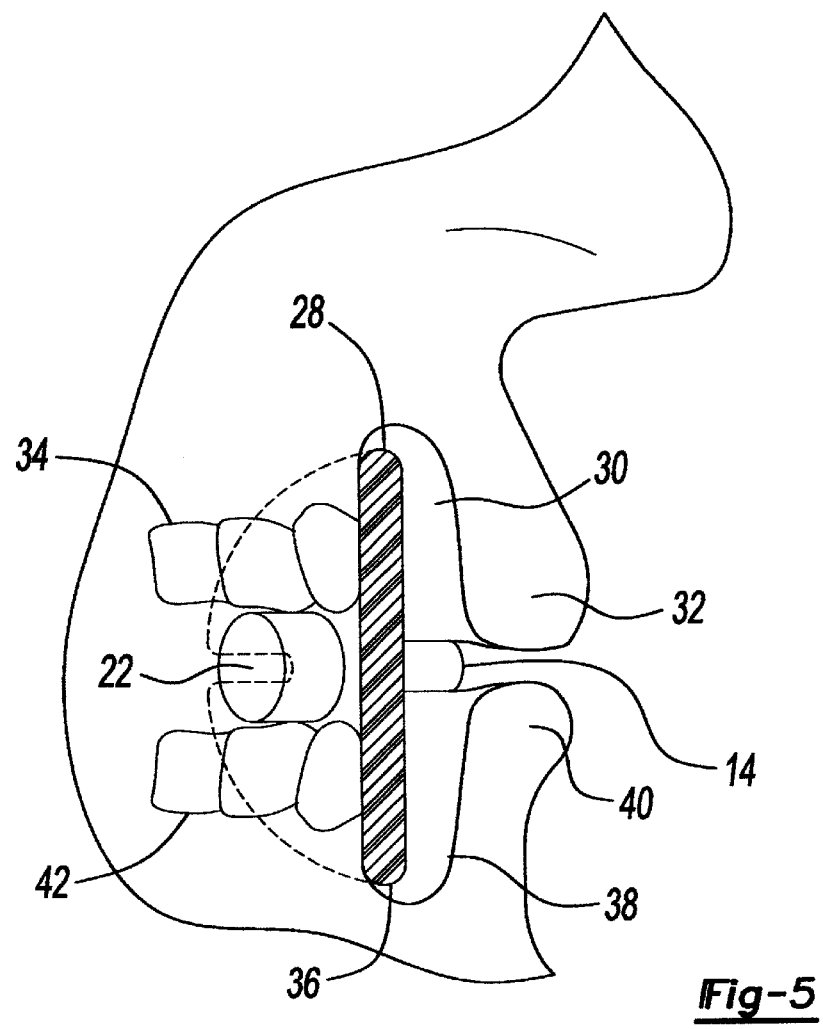
FIG. 5 is a view showing the breathing control device positioned relative to a partial profile of the face of the user taken on irregular line 4—4 in FIG. 2.

Referring to the drawings a breathing control device embodying the invention is designated generally at 10 includes a body member 12 made of a relatively flexible plastic material intended to be disposed in the mouth between the lips and teeth. The body member 12 is in the form of a flat sheet in a vertical direction but is curved in a horizontal direction as in the wall of a cylinder. The curved sheet is in the form of an elongated oval slightly larger than the closed mouth of a user as seen in FIG. 4. Guide members in the form of pegs 14 are disposed in horizontally spaced relation to each other and near opposite side edges 16 of the body member 12 to extend perpendicular to the convex surface 18 of the curved sheet. The curved sheet or body member 12 also is provided with a pair of openings or slots 20 extending in opposite direction away from the pegs 14 to the side edges 16. A pair of pegs 22 also extends inwardly from the opposite or concave side 24 of the curved sheet. The pegs 22 can be of the same diameter as the pegs 14 as seen in FIGS. 2 and 3 or they can have a larger diameter as seen in FIG. 5. If desired, the pegs 22 can be flat on opposed surfaces since only the upper and lower surfaces are gripped between the teeth.

The device 10 is placed within the mouth and as seen in FIG. 5 its upper edge 28 is disposed in the upper-space 30 formed between the upper lip 32 and upper teeth 34 and the lower edge 36 of the body member 12 is disposed in the lower space 38 formed between the lower lip 40 and the lower teeth 42. The body member 12 is such that the spacing of the upper and lower edges 28, 36 are smaller than the spacing than the top of upper space 30 and the bottom of the lower space 38 so that the body member 12 does not engage the tops and bottoms of the spaces 38 to avoid discomfort. The body member 12 also extends so that the opposite side edges 16 are within and spaced outwardly of the side edges of the closed mouth. When disposed within the mouth, the pair of pegs 14 extend outwardly from the convex surface 18 and positioned at the corners of the mouth to prevent lateral or side-to-side displacement of the body member 12 from its position within the mouth. The pegs 14 also act as handles for manipulating the device 10 when placing it within the mouth. The inner pegs 22 typically are gripped between the teeth and act to prevent vertical displacement of the body member 12 and also to prevent contact of the teeth and therefore grinding or gnashing of teeth during sleep.

When disposed in the mouth, the body member 12 has its concave surface 24 against the front of the teeth 34 and 42. Any amount of air passing through the mouth tends to cause the body member 12 to be pressed against the teeth and gums. The positioning of the body member 12 within the mouth also tends to stimulate secretion of saliva that must be disposed of by swallowing. The swallowing of saliva has the beneficial effect of tending to neutralize the acid reflux phenomenon. The air required for swallowing is facilitated by admission of air through the corners of the mouth and through openings 20 in device 10 that extend in opposite directions from near the two stop elements or pegs 14. When swallowing occurs, lips part slightly at the outer corners and permit the admission of the required air through the openings 20. The openings 20 extend from the perimeter of the device 10 toward a point close to but spaced from the guide members or pegs 14. In actual practice the device 10 can be provided with slots 20 more widely spaced than shown in the drawings so that the user can elongate the slots to a length to adjust the amount of air admitted upon swallowing. The longer the slot the more air is admitted. Such air is useful in rapidly dispersing accumulated saliva in the mouth.

The device 10 can be molded as a unit of any of a variety of plastic materials that can be tolerated by the mouth and can formed from a stiff but flexible plastic material so that it can flex from its as-molded condition to conform to the curvature of the facial area of a user.

It has been found that different size pegs 22 can be used on the inside concave surface 24 of the body member to accommodate slightly different spacing of the upper and lower teeth. This can easily be accommodated in manufacture by selected inserts in the mold.

When the device 10 is first placed in the mouth as seen in FIGS. 4 and 5, free air passage through the mouth is prevented and directed through the nasal passages. This appears to cause a vacuum behind the mouthpiece. Upon swallowing the slight opening of the corners of the mouth cause a rapid air passage through the open ended slots 20 extending from the guide pegs 14 that moves the accumulated saliva from the area.

The device 10 acts as an air valve to control the flow of air through the mouth. Flow through the mouth is normally prevented and breathing is redirected through the nose. This alone is beneficial to prevent snoring. Although airflow is usually prevented through the mouth, the act of swallowing causes the corners of the mouth to open slightly and permit the admission of air through the openings 20 at the opposite sides of the peg elements 14. The act of swallowing permits the passage of saliva from the mouth area to the throat where it can neutralize acid reflux symptoms.

Although the device 10 is contemplated for use during sleep to alleviate snoring, teeth grinding and acid reflux that may become aggravated during the usual horizontal sleep position, it should be noted that the device has utility during waking hours. In an active upright or seated position while awake and engaged in such activities as reading, watching television or driving an automobile, the device may be used to combat acid reflux by the stimulation and swallowing of saliva.

A breathing control device has been provided which can be inserted and comfortably held within the mouth that acts as a valve to control air passage through the mouth. Upon inhaling, airflow through the mouth is prevented and redirected through the nasal passages to inhibit snoring. Limited air passage is permitted at the corners of the mouth to aid the swallowing of saliva to neutralize acid reflux. Provision also is made for holding the device in position by means that reduce grinding of teeth during sleep. The device also has useful application when awake for stimulating and swallowing saliva to minimize the effect of acid reflux.

I claim:

1. A breathing control device for insertion in the mouth between the lips and gums, comprising:
   a body member of flexible sheet material having a generally oval shape and being larger than a persons mouth with concavo-convex faces conforming generally to the curvature of a persons mouth area with the concave face abutting the teeth and the convex face abutting the interior of the lips, said body member acting to stimulate the salivary glands and prevent air passage through the mouth of the user except for swallowing and to direct air through the nose;
   a pair of stop elements spaced apart and extending normal to the convex face at opposite ends of said body member and at opposite sides of the mouth, said stop elements limiting lateral movement of said body member in the mouth; and
   a pair of openings formed by said body member and disposed at opposite side edges of said body member for permitting limited air passage at the corners of the mouth upon swallowing of saliva.

2. The breathing control device of claim 1 wherein said pair of openings formed by said body member extend between opposite ones of said concavo-convex faces.

3. A breathing control device for insertion in the mouth between the lips and gums, comprising:
   a body member of flexible sheet material having a generally oval shape and being larger than a persons mouth with concavo-convex faces conforming generally to the curvature of a persons mouth area with the concave face abutting the teeth and the convex face abutting the interior of the lips, said body member acting to stimulate the salivary glands and prevent air passage through the mouth of the user for directing air through the nose;
   a pair of stop elements spaced apart and extending normal to the convex face at opposite ends of said body member and at opposite sides of the mouth, said stop elements limiting lateral movement of said body member in the mouth; and
   a pair of openings formed by said body member and disposed at opposite side edges of said body member for permitting limited air passage at the corners of the mouth upon swallowing of saliva, said openings extending from a point spaced from said stop elements and through said side edges.

4. The breathing control device of claim 3 wherein said pair of stop elements is in the form of a pair of pegs extending to the exterior of the mouth.

5. The breathing control device of claim 4 and further comprising a second pair of pegs extending from said concave surface and are in position for gripping by the teeth of the user.

6. The breathing control device of claim 5 wherein said second pair of pegs are in axial alignment with said first mentioned pegs.

7. The breathing control device of claim 5 where said second pair of pegs are larger than said first mentioned pegs.

8. A breathing control device for insertion in the mouth between the lips and gums, comprising:
   a body member of flexible sheet material having a generally oval perimeter and being larger than a persons mouth, said body member conforming generally to the curvature of a persons mouth area with a first side facing the gums and a second side facing the interior of the lips, said body member acting to stimulate the salivary glands and limiting air passage through the mouth so that air is directed through the nose;

a pair of guide elements spaced apart and extending outwardly from said first side of said body member at opposite sides of the mouth said guide elements limiting vertical and horizontal displacement of said body member relative to the mouth; and a pair of openings formed by said body member and disposed between said guide elements and the ends of said body member, respectively, said openings permitting limited air passage at the corners of the mouth upon swallowing of saliva.

9. The breathing control device of claim 8 wherein said guide elements extend substantially normal to said first side of said body member.

10. The breathing control device of claim 9 wherein said guide elements extend to the exterior of the users mouth to form handles for positioning said body member.

11. The breathing control device of claim 9 wherein a second pair of guide elements extend inwardly from said second side of said body member in position for gripping by the teeth of the user to limit vertical movement of said body member and prevent grinding of teeth.

12. The breathing control device of claim 11 wherein said guide elements are pegs and said second pair of guide elements is in axial alignment with said first mentioned pair of guide elements.

13. The breathing control device of claim 12 wherein said pair of guide elements protrude through said body member and extend sufficiently for gripping by the teeth.

14. The breathing control device of claim 8 wherein said openings are elongated and extend radially in opposite directions away from said guide elements.

15. The breathing control device of claim 8 wherein said openings extend from a point slightly spaced from said guide elements to and through the perimeter of said body member.

* * * * *